United States Patent [19]

Ho

[11] Patent Number: 4,463,194
[45] Date of Patent: Jul. 31, 1984

[54] PROCESS FOR MAKING PIPERITONE FROM PLINOLS

[75] Inventor: Tse-Lok Ho, Jacksonville, Fla.

[73] Assignee: SCM Corporation, New York, N.Y.

[21] Appl. No.: 444,887

[22] Filed: Nov. 29, 1982

Related U.S. Application Data

[63] Continuation-in-part of Ser. No. 352,787, Feb. 26, 1982, abandoned.

[51] Int. Cl.$^3$ ............................................. C07C 45/45
[52] U.S. Cl. ................................ 568/343; 568/838; 568/386; 568/353; 585/357
[58] Field of Search ............... 568/836, 838, 357, 380, 568/343, 353; 585/357

[56] References Cited

U.S. PATENT DOCUMENTS

| | | | |
|---|---|---|---|
| 2,237,980 | 4/1941 | Blagden et al. | 260/587 |
| 2,387,587 | 10/1945 | Hunsdiecker | 260/586 |
| 2,526,171 | 10/1950 | Stoll | 260/586 |
| 2,946,823 | 7/1960 | Eschinazi | 260/593 |
| 3,781,314 | 12/1973 | Bollag et al. | 260/410.9 |
| 3,960,970 | 6/1976 | Pasedach et al. | 260/631 |
| 4,058,572 | 11/1977 | Kane et al. | 260/631.5 |

OTHER PUBLICATIONS

Anderson et al, "Azulene. I. An Improved Synthesis", JACS, 73, pp. 232–235 (1951).
Marshall et al, "Total Synthesis of Racemic Conessine", JACS, 84, pp. 1485–1486 (1962).
Kutney et al, "A Totally Synthetic Entry into the Veratrum Alkaloid Skeleton", Tetrahedron Letter No. 33, pp. 2911–2918, 1965 Pergamon Press Ltd.
Organic Reaction, vol. 16, pp. 47–58 (1968), "The Aldol Condensation".
Johnson et al, "Acetylenic Bond Participation in Biogenetic-Like Olefinic Cyclizations, II, Synthesis of dl-Progesterone", JACS, vol. 93, pp. 4322–4334, (1971).
Streitwieser et al, "Introduction to Organic Chemistry" (1976), pp. 272–275; 276; 290–292.
Fieser et al, "Reagents for Organic Synthesis", pp. 498–499, (1967).

Primary Examiner—James H. Reamer
Attorney, Agent, or Firm—R. A. Sturges; M. H. Douthitt

[57] ABSTRACT

A process for making piperitone from crude plinols involving hydrogenating the crude plinols to form dihydroplinols and dehydrating the dihydroplinols to yield an iridene. The iridene is then oxidatively cleaved at the unsaturation to form an acyclic dione. The dione is cyclized in the presence of a base to form piperitone.

5 Claims, 1 Drawing Figure

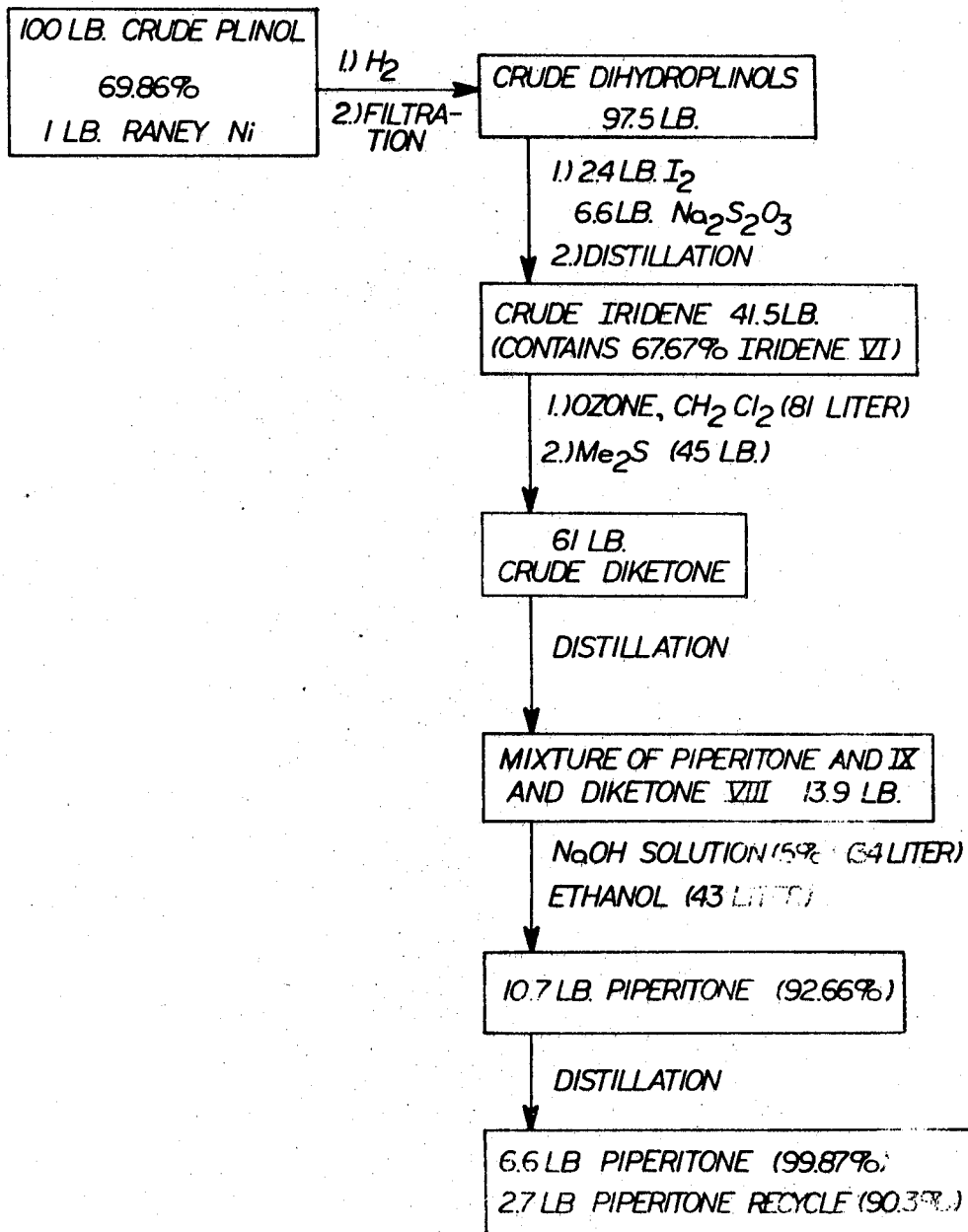

PROCESS FOR MAKING PIPERITONE FROM PLINOLS

RELATED APPLICATION

This application is a continuation-in-part of my copending application Ser. No. 352,787 filed Feb. 26, 1982, now abandoned.

This invention relates as indicated to a process for making piperitone from plinols via a cyclomutation sequence. More particularly, this invention involves hydrogenating crude plinols which is normally a waste product, dehydrating the dihydroplinols to yield the hydrocarbon, iridene, oxidatively cleaving the iridene ring to yield the corresponding dione and cyclizing the dione to form piperitone. The ring carbon atom content of the ketone is augmented. Plinols currently constitute a major loss in the preparation of linalool by pyrolysis of pinanols. These can, by this process, be effectively converted to pipertone which is useful in room air fresheners, for odor masking purposes, and in flavor compositions.

BACKGROUND OF THE INVENTION AND PRIOR ART

In the manufacture of linalool from pinanol (III) by pyrolysis of the latter, plinols constitute the major loss. Plinols which are monocyclic compounds (1,2-dimethyl-3-isopropenyl cyclopentanols) (I) are obtained from an intramolecular -ene reaction of linalool (II) (Ikeda et al, J. Chem. Soc. Jap. 57, page 425 (1936); CA 30, 5937 (1936)). According to Ohloff et al, Helv. Chim. Acta 50, 759 (1967), the above reaction yields four plinol isomers in the approximate percentages indicated in the following equation:

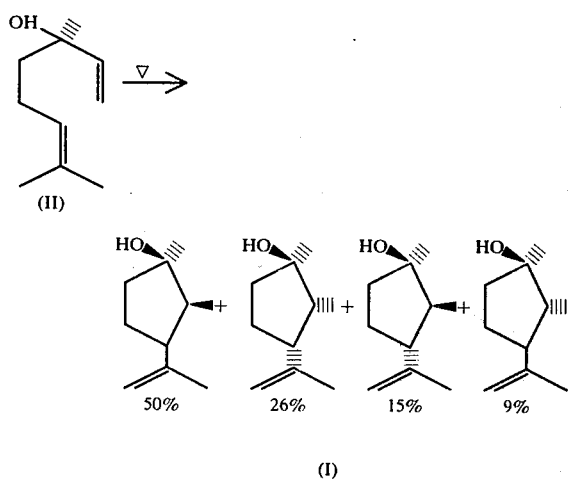

The formation of plinols from linalool in the pyrolysis reaction cannot be avoided because the activation energy for this secondary reaction is lower than that of linalool generation. The amount of this "waste" is substantial. At the outset of this work, no practical utility for the plinols had been found other than as a fuel supplement.

Pipertone (IV) occurs in a variety of eucalyptus oils. Hydrogenation of piperitone (IV) furnishes menthone which is readily converted to menthol. Thus a process productive of piperitone represents also a portion of a menthol process.

It has now been found that piperitone (IV), can be prepared from plinols by a cyclomutation sequence whereby what was normally a waste product, is convertable to a material useful, for example, as a precursor to menthone, or mixed isomeric menthols by hydrogenation.

As will be seen from the following disclosure, the unit organic operations employed herein include hydrogenation, dehydration, oxidative cleaving of an unsaturated ring, cyclization and dehydration in that order. Hydrogenation is a well known unit organic operation, and the catalysts and conditions of temperature and pressure useful in effecting the addition of hydrogen to unsaturates are well known. (See Streitwieser et al "Introduction to Organic Chemistry" 1976, page 276). Dehydration to move the formerly external unsaturation into the ring is also known per se. (See ibid p. 272-275). Ozonolysis is also a known unit organic operation (See ibid pages 290-292). Mutative cyclization and dehydration of an aliphatic dione with an alcoholic solution of a strong base is also known (See "Organic Reactions", Volume 16, Pages 49-58).

Reference may also be had to Kutney et al, Tetrahedron Letters, 2911 (1965) Anderson et al, JACS, 73, p 232 (1951); Johnson et al, JACS 93, p. 4332 (1971); and Marshall et al, JACS 84, p. 1485 (1962) showing certain of the operations in sequence as applied to polycyclic materials, e.g., alkaloids, decahydro-2-naphthtol-1, production of progesterone from a trienynol, and synthesis to a cyclic olefin which is oxidized and then cyclized via an aldol condensation. Regarding the general scheme of the invention, related transformations may be found in the above Kutney et al reference. However, there is nothing in the literature that suggests the application of the present multi-step process to the synthesis of piperitone from plinols. Piperitone produced in accordance herewith may be hydrogenated according to the procedure described by Blagden et al in U.S. Pat. No. 2,237,980.

BRIEF STATEMENT OF THE INVENTION

Briefly stated, the present invention is in a cyclomutation sequence applied to plinols which are characterized by alkyl substituents directly attached to ring carbon atom and having 5 ring carbon atoms. According to the invention, the plinols are first hydrogenated and then dehydrated to yield an internally unsaturated iridene hydrocarbon, i.e., having unsaturation in the ring. The iridene is then oxidatively cleaved at the ring unsaturation to form the corresponding dione. The dione is then cyclized in the presence of a base to form piperitone having 6 carbon atom in the ring instead of the original 5.

BRIEF DESCRIPTION OF THE DRAWINGS

The annexed drawing is a flow sheet illustrating a preferred cyclomutation sequence for converting plinols to piperitone.

DETAILED DESCRIPTION

For ease of reference, the following structures will be understood when referred to in the text by the associated Roman numeral:

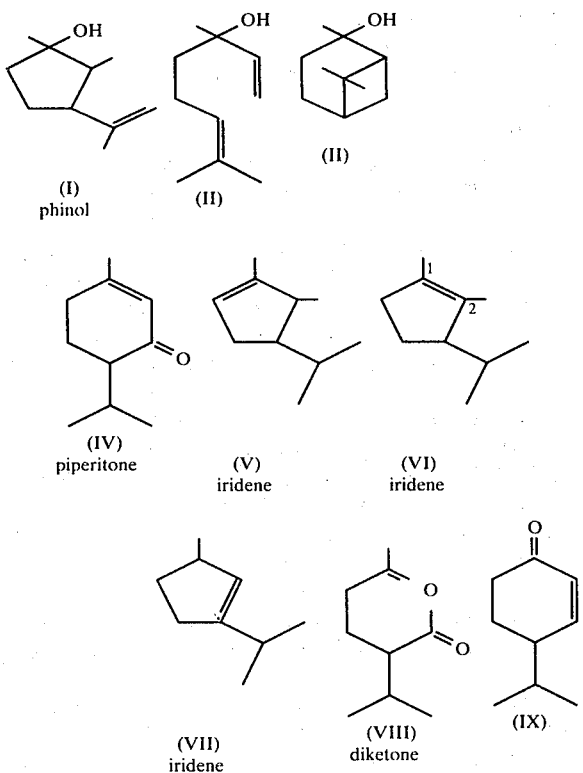

The cyclomutation sequence of the present invention may be better understood by having references to the annexed drawing illustrating a flow sheet of the process as applied to plinols derived from a linalool process as mentioned above. 100 pounds of a linalool distillate rich in plinols (I) were hydrogenated using one pound of Raney nickel catalyst under 100-500 psig pressure and at a temperature of 25°-60° C. resulting in a mixture of dihydroplinols and tetrahydrolinalool. Rather surprisingly, much of the tetrahydrolinalool formed a gel which could be separated from the dihydroplinols by decantation. However, filtration is preferred, and the gel is thereby broken. In the example, 97.5 pounds of the crude dihydroplinols were recovered.

Departing briefly from the drawing, dehydration of the dihydroplinol mixture may be accomplished with a protic acid, $H_2SO_4$ (dilute) to yield the iridenes (V), (VI) and (VII). Both (V) and (VI) are formed rapidly in approximately equal amounts. As time elapsed, however, an increase in (VI) and the appearance of (VII) were observed. At equilibrium the ratio of (VI) to (VII) was about 7:3.

For the synthesis of piperitone, only (VI) is the useful iridene. Although (VI) and (VII) could be separated by distillation in a spinning band column, maximum production of (VI) is desired. It was then found that dehydration of the dihydroplinol mixture with a catalytic quantity of iodine gives rise to a mixture of (VI) and (VII) in a ratio of 9:1. This variation is shown in the flow sheet.

Thus, 2.4 pounds of iodine were added to the crude dihydroplinol mixture (97.5 parts) and heated to obtain from the reaction mixture 41.5 parts of crude iridene containing 67.67% iridene (VI). Iridenes are internally unsaturated compounds wherein the unsaturation is between ring carbon atoms. Thereafter, 6.6 pounds of sodium thiosulfate were then added to combine with the iodine.

The reaction can be carried out between 50°-200° C. At higher temperature, reaction proceeds faster. A non-hydroxylic solvent may be used as diluent. DMF, DMSO are suitable. Although the use of iodine for dehydration has been known prior to our work, these precedents could not have been used to predict the outcome of giving more than statistical distribution of the various olefins (there are theoretically nine possible isomers, discounting optical isomers).

The high (9:1) ratio of iridene (VI) to iridene (VII) was not predictable, as both isomers contains a tetracyclic double bond in a five-membered ring. On the basis of thermodynamic evaluation, it would not be possible to forecast a ratio of higher than 6:4 in favor of either (VI) or (VII).

The selective procurement of iridene (VI) facilitated its conversion into piperitone in two steps. Accordingly, the iridene (VI) was first oxidatively cleaved to yield the diketone (VIII) and secondly cyclized with alkali. In the example illustrated in the drawing, the iridene was dissolved in methylene chloride (81 liters) and ozone bubbled through. Thereafter, 45 pounds of dimethyl sulphide were added. The resulting crude (61 lbs.) diketone (VIII) was distilled and recovered. The distillate contained some piperitone as well as the cyclohexenone (IX) and diketone (VIII). This distillate (13.9 lbs.) was treated with a mixture of 34 liters of 5% NaOH and 43 liters of ethanol to dehydratively cyclize the diketone. After distillation, a total of 9.3 lbs. of piperitone was recovered, part of which is recycled.

In effecting the hydrogenation of the double bonds in the plinols starting material, any of the known methods of hydrogenation with molecular hydrogen such as mentioned above may be used. Thus, liquid phase or vapor phase hydrogenation in the presence of a suitable hydrogenation catalyst, e.g., a solid contact catalyst may be used. I prefer, for mainly economic and handling reasons to utilize liquid phase hydrogenation with molecular hydrogen in the presence of a solid contact catalyst such as nickel, palladium/alumina, palladized charcoal, platinum, rhodium, ruthenium as fine dispersions, or coated on a suitable support such as alumina, e.g., platinum/alumina, or the like catalysts which are well known. (See Streitwieser "Introduction to Organic Chemistry" (1976) page 276 et seq.). Usually hydrogenation reactions are usually carried out under superatmospheric pressure, e.g., from 1.1 to 500 atmospheres, preferably between 100 and 500 psig and at a suitable temperature, e.g., $-10°$ to 250° C., preferably 25° to 60° C. Hydrogenation of crude plinols results in the formation of dihydroplinols.

In effecting dehydration of the dihydroplinols to form iridenes, any of the known methods of catalytically removing water from the molecule of an organic cyclic alcohol may be used. The dehydration can be performed at room temperature to 150° C., preferably 80° to 120° C. where convenient rates of dehydration-equilibration are observed. Catalytic dehydration in the presence of iodine at reflux or a dehydrating agent such as a protic acid for example, mineral acid, e.g., sulfuric acid, phosphonic acid phosphoric acid, $P_2O_5$, hydrochloric acid, hydrobromic, nitric, etc., are well known. Refluxing with iodine followed by removal of the catalyst, e.g., with a water soluble iodine reactant, e.g., sodium thiosulfate followed by drying is a preferred mode of dehydrating the dihydroplinols. Reference may be had to Fieser et al "Reagents for Organic Synthesis" page 498–499 (1967) and Streitweiser, "Introduction to Organic Chemistry" (1976), pp. 272-275 for other dehydration procedures useful herein. The product of the dehydration step is a mixture of iridines (V), (VI) and (VII).

In effecting oxidative cleavage of the iridenes to form a diketone (VIII), this reaction is usually carried out in the liquid phase with ozone at a low temperature from just above the freezing point of the iridene mixture to no more than about 25° C., desirably in the range of $-10°$ C. to $-80°$ C. and preferably at about $-70°$ C. Suitable conditions for ozonolysis are shown in Streitwieser et al, supra at pages 290-291 and by Eschinazi U.S. Pat. No. 2,946,832. An inert solvent may be used, e.g., ether, a haloalkane, for example, methylene chloride, chloroform, a lower alcohol, e.g., ethyl alcohol, a lower carboxylic ester, e.g., ethyl acetate or a lower carboxylic acid, e.g., acetic acid. This reaction is usually and conveniently carried out at atmospheric pressure although superatmospheric pressure may be used, if desired. The product of oxidative cleavage is a diketone (VIII).

Cyclization of a diketone is also a well known organic reaction as shown by Hunsdiecker, U.S. Pat. No. 2,387,587. Stoll U.S. Pat. No. 2,526,171 and Fieser et al "Reagents for Organic Synthesis" pp. 498-99. The cyclization is conveniently carried out herein by any of the procedures suggested by Hunsdiecker, Supra. (in connection with different diketones) in Columns 2 and 3 beginning at line 10 of Column 2 and carrying over to Column 3, line 13. Thus, cyclization of the diketone may be done in the presence of a catalytic amount (e.g., from 0.05% to 5% by wt.) of an alkaline condensation reagent, preferably alcoholic alkali metal hydroxide, carbonate or bicarbonate or alkaline earth metal hydroxide, carbonate or bicarbonate. Especially suitable are ethyl alcoholic- or methyl alcoholic-potassium hydroxide, ethyl alcoholic- or methyl alcoholic-sodium hydroxide, or ethyl alcoholic- or methyl alcoholic-barium hydroxide solution; alkali alcoholates, e.g., sodium ethylate or potassium ethylate.

It should be noted that cyclodehydration of diketones is effected by acidic or basic catalysts. The occurrence of an uncommon, if not unique, thermal cyclization (during distillation) was observed. Thus, it was for the purpose of ensuring complete conversion to piperitone that treatment with dilute alkali was instituted. Besides sodium hydroxide, sodium carbonate, lithium hydroxide, potassium hydroxide, barium hydroxide are also useful catalyst. Alcoholic or aqueous solutions could be used. Temperatures between 0° to 150° are most convenient for accomplishing the transformation.

The diketone (VIII) can be made directly from dihydroplinol by chromic oxidation.

Operationally, the best mode of carrying out my invention is to hydrogenate the crude plinols as in Example I with a contact hydrogenation catalyst, especially Raney nickel. Thereafter, the resulting crude dihydrophenols are dehydrated in the presence of a catalyst (iodine) as in Example IIa and the resulting iridenes rapidly distilled off. The iridenes are then oxidatively cleaved as in Example III to open the ring by ozonolysis followed by treatment with a dialkyl sulfide, e.g., dimethyl sulfide or diethyl sulfide. The resulting diketone is cyclodehydrated, as in Example IV preferably with a dilute alcohol solution of an alkali metal hydroxide, such as KOH, LiOH and preferably NaOH. This is followed by distillation to yield the final piperitone (IV) product in good yield and purity (99.87%). Partial conversion of the ozonized product (diketone (VIII)) to piperitone was observed during the first distillation. Isomeric cyclohexenone (IX) produced as a minor by-product (IV:IX=93:7) in the final step is cleanly separated from piperitone (IV) by distillation.

Structural confirmation of the ketone (IX) was obtained by gas chromatography and spectral comparison of a sample obtained from treatment of cis-verbanone with sulfuric acid.

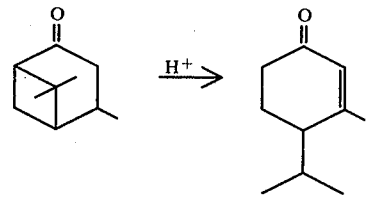

It is quite surprising that a ratio of 93 parts of piperitone to 7 parts of alkyl substituted cyclohexanone is obtained. The mechanism is represented by the following:

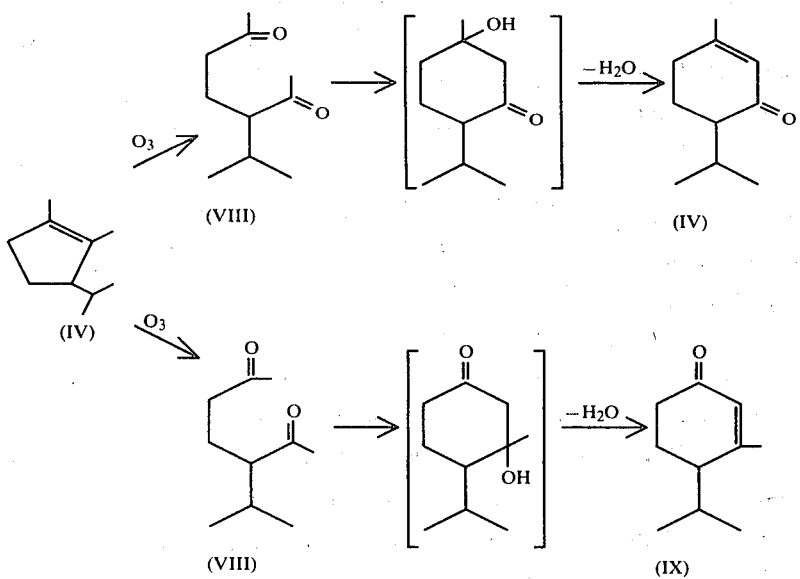

In the above formula, the dione VIII is the same material, just drawn differently to indicate from which methyl group the hydrogen is transferred. Steric hindrance might account for some predominance of IV over IX, but not anywhere near a 12 to 1 ratio as here achieved.

The following are examples of the steps of my invention.

EXAMPLE I

Dihydroplinols

A suspension of 8 grams of Raney nickel catalyst in 800 grams of crude plinols (69.86% plinols) was hydrogenated in a two liter autoclave at 40° C. and 100–500 psig. The reaction was monitored by NMR spectroscopy and after 28 hours, was terminated when no olefinic signal was detected. The autoclave was opened and the catalyst removed by filtration. The filtrate weighed 780 grams.

EXAMPLE II

Dehydration of the Dihydroplinols (IIa) Iodine as Catalyst:

A mixture of 740 grams of dihydroplinols obtained in Example I was heated in the presence of 18 grams of iodine under reflux for ten days. The reaction was monitored by gas chromatography. The solution was cooled, 50 grams of sodium thiosulfate added, and the mixture stirred vigorously. An oily layer was separated and further washed with sodium thiosulfate solution and the oily layer dried over anhydrous sodium sulfate. The crude product weighed 679 grams. Distillation yielded 537 grams of mixed iridenes—bp. 98° C./100 torr. Fractions were blended to give 315 grams of oil containing 67.67% iridene (VI).

(IIb) Iodine as Catalyst—small scale:

A mixture of 120 mg of iodine and 15 g. of dihydroplinols was heated under reflux in an oil bath for 4 days. Gas chromatography (GC) analysis showed the mixture contained iridene (VII) 5.86%; iridene (V) 13.76%; and iridene (VI) 51.52%. The ratio of (VI) to (VII) was 9:1. Distillation of the crude mixture gave 8.6 grams of a colorless oil (bp 74° C./36 Torr). GC showed the oil contained iridene (VII) 9.71%; iridene (V) 3.81%; and iridene (VI) 50.22%.

(IIc) Sulfuric acid as catalyst:

A mixture of 5.1 g of dihydroplinols and 50 ml of 50% sulfuric acid was vigorously stirred at room temperature for 17 hours. The reaction mixture was extracted with pentane. The pentane extract was washed with water, saturated brine, dried over anhydrous $Na_2SO_4$ and concentrated in vacuo to give 4.4 g (98% theory yield) of a yellow oil. GC showed it contained iridene (VII) (15.7%), iridene (V) (1.88%) and iridene (VI) (42.58%).

EXAMPLE III

Ozonolysis of Iridene (VI)

A solution of 116 g iridene mixture containing 67.67% of iridene (VI) was dissolved in 500 ml of methylene chloride. Ozone was passed through the solution via a fritted gas inlet tube at −70° C. After 12 hrs., the solution became blue and reaction was terminated. Excess ozone was removed by nitrogen. Dimethyl sulfide (150 ml) was added dropwise at −70° C. and stirred at autogeneous temperature for 15 hours. The solution was washed three times with water (900 ml), dried over anhydrous sodium sulfate and concentrated to yield 171.6 g of oil.

Spinning band distillation of the crude product gave the following results:

|  |  | Lights | | |
|---|---|---|---|---|
|  |  | Piperitone (IV) | | Diketone (VIII) |
| Fraction 1–3 | 15.7 g | | | |
| Fraction 4 | 4.7 g | 1.1* g | 23.68% | 1.6 g 34.28% |
| Fraction 5 | 5.0 g | 2.7 g | 53.27% | 0.8 g 29.17% |
| Fraction 6 | 7.1 g | 5.0 g | 70.81% | 0.7 g 10.10% |
| Fraction 7 | 5.7 g | 4.4 g | 77.06% | 0.9 g 16.10% |
| Fraction 8 | 5.2 g | 3.9 g | 74.47% | 0.4 g 6.79% |
| Fraction 9 | 5.2 g | 4.2 g | 81.61% | 0.3 g 6.40% |
| Fraction 10 | 5.7 g | 3.8 g | 66.72% | 0.4 g 7.14% |
| Fraction 11 | 4.6 g | 3.7 g | 79.6% | 0.6 g 13.06% |
| Fraction 12 | 5.3 g | 1.7 g | 32.38% | 2.2 g 41.2% |
| Fraction 13 | 0.7 g | 0.6 g | 7.92% | 0.3 g 37.97% |
| Residue | 22.8 g | Total Yield | | Total Yield |

| Lights | |
|---|---|
| Piperitone (IV) | Diketone (VIII) |
| 30.56** g | 8.2 g |

*Rounded to 1 place.
**Accurate to 2 places.

Combined yield of piperitone (IV) and diketone (VIII) corresponded to 44% theory yield of ozonolysis product (VIII).

EXAMPLE IV

Piperitone (1) To cyclize the diketone moiety, a solution of 37 g of the mixture of piperitone (IV) and diketone (VIII) (vide supra) in 250 ml of ethanol and 200 ml of 5% NaOH was heated on an oil bath at 100° C. for 4 hrs. After cooling, the reaction mixture was extracted with ether. The ether extracts were combined and stripped to give 28.5 g of colorless oil. GC showed it contained 92.66% of piperitone (IV) and 5.22% of an isomeric alpha, beta-unsaturated ketone (IX).

(2) A sample of 53.7 g of piperitone (92.27%) was distilled on a spinning band column to give the following results:

| Fraction 1 | 3.0 g | Piperitone 87.42% (2.6 g) |
|---|---|---|
| Fractions 2–12 | 33.1 g | Piperitone blended 99.87% (33 g) |
| Fractions 13–15 | 10.4 g | Piperitone 91.49% |
| | | Isomeric Ketone 7.51% (9.5 g) |
| Fraction 16 | 2.7 g | Piperitone 6.14% |
| | | Isomeric Ketone 90.31% (0.2 g) |
| Total Piperitone | 45.3 g | (Fractions 1 to 15) |
| | | or 92% recovery from piperitone contained in distillation charge. |
| (3) Characterization of isomeric ketone (IX) | | |
| IR (film) | 1680, 1620 cm$^{-1}$ | |
| NMR (CDCl$_3$) | δ 0.8 (3H, d, J = 6), 1.0 (3H, d, J = 6) | |
| | 1.97 (3H, d, J = 1), 2.0–2.5 (6H, m), 5.90 | |
| | (1H, q, J = 1) | |
| MS | 41 (34%), 43 (47%), 67 (18%), 81 (26%), | |
| | 95 (99%), 109 (76%), 110 (100%), 152 | |
| | (45%, M$^+$). | |

What is claimed is:

1. The process of making piperitone comprising the steps of hydrogenating a crude plinol in the presence of a contact catalyst at a pressure of 100–500 psig to form dihydroplinol, dehydrating the dihydroplinol by heating in the presence of a dehydration catalyst to yield iridene, oxidatively cleaving the alicyclic ring of said iridene with ozone at said unsaturation to form the corresponding diketone, and cyclizing said diketone in the presence of alkali to form piperitone.

2. A process as defined in claim 1 in which the oxidative cleaving step is carried out with ozone.

3. A process as defined in claim 1 in which the oxidative cleaving step is carried out with chromic acid.

4. The process of claim 1 further characterized by step of hydrogenating the piperitone to form menthone.

5. A process of making piperitone comprising the steps of hydrogenating a crude plinol in the presence of about 1% by weight of Raney Nickel with molecular hydrogen at a pressure of 100–500 psig and a temperature of 25° to 60° C., for a period of time until the unsaturation in the crude plinol has been satisfied to obtain dihydroplinol; dehydrating the dihydroplinol by heating under reflux and in the presence of a dehydration catalyst for a period of time sufficient to form a mixture of iridenes, distilling the mixture to recover a distilled iridene mixture, treating said distilled iridene mixture with ozone in an inert solvent at a temperature in the range of 10° C. to −80° C. to until the solution indicates completion of the reaction by color change, and cyclizing the diketone moiety by reluxing with alcoholic solution containing a catalytic amount of an alkali metal hydroxide to covert said diketone moiety to piperitone and recovering piperitone from the reaction mass.

* * * * *